US006844884B2

(12) United States Patent
Balloni et al.

(10) Patent No.: US 6,844,884 B2
(45) Date of Patent: Jan. 18, 2005

(54) MULTI-PLANE GRAPHIC PRESCRIPTION INTERFACE AND METHOD

(75) Inventors: William Balloni, Menomonee Falls, WI (US); Kristine Gould, Delafield, WI (US); Yawar Murad, Schaumberg, IL (US); Bipin Salunkhe, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 408 days.

(21) Appl. No.: 09/748,929

(22) Filed: Dec. 27, 2000

(65) Prior Publication Data

US 2002/0082494 A1 Jun. 27, 2002

(51) Int. Cl.[7] ............................................. G09G 15/00
(52) U.S. Cl. ...................................... 345/629; 345/630
(58) Field of Search ................................. 345/157, 419, 345/420, 423, 424, 427, 629, 630; 324/307, 309; 600/410, 411, 425, 427; 382/128, 131

(56) References Cited

U.S. PATENT DOCUMENTS

| | | | | |
|---|---|---|---|---|
| 6,108,573 A | * | 8/2000 | Debbins et al. | 345/629 |
| 6,379,302 B1 | * | 4/2002 | Kessman et al. | 600/437 |
| 6,396,266 B1 | * | 5/2002 | Debbins et al. | 324/307 |
| 6,484,048 B1 | * | 11/2002 | Hoshino et al. | 600/410 |
| 6,529,766 B1 | * | 3/2003 | Guendel | 600/427 |
| 6,563,941 B1 | * | 5/2003 | O'Donnell et al. | 382/131 |

OTHER PUBLICATIONS

Jean et al ("Automated Atlas Integration and Interactive Three–Dimensional Visualization Tools for Planning and Guidance in Functional Neurosurgery": 1998 IEEE—0278–0062/98).*

Robb, Richard A., Three–Dimensional Visualization in Medicine and Biology, Handbook of Medical Imaging, ISBN 0–12–077790–8, Sep. 1, 2000, pp. 685–712, Academic Press, San Diego.

Analyze 3.0 User Manual, retrieved from the internet: http://www.bmtp.akh–wien.ac.at/people/backwe1/HSL/HelpDocs/AlalyzeAVW.html on Feb. 16, 2004, 11 pages.

European Search Report for Application No. EP 01 31 0701, dated Mar. 2, 2004, 3 pages.

"Gyrex 2T Prestige™" High Field MRI System Operation Manual, Elscint Cat. No. 490–6321–0527; Version 3.0; 16–pg. document; by *Elscint Ltd.* (Mar. 1998).

Elscint Prestige Screen Shots; 2–pg. document (Mar. 13, 2000).

"Signa® Profile™ Reference Manual Scan"; 2256981–100; Revision 0; by General Electric Co.; pp. 7–313 to 7–342; (Mar. 2000).

Signa Profile Screen Shots; 3–pg. document (Jun. 10, 1999).

* cited by examiner

*Primary Examiner*—Mark Zimmerman
*Assistant Examiner*—Enrique L. Santiago
(74) *Attorney, Agent, or Firm*—Foley & Lardner LLP

(57) ABSTRACT

A method of acquiring a graphic prescription from an operator of an imaging device comprises displaying a first two-dimensional view of a first localizer image and a second two-dimensional view of a second localizer image, and displaying a three-dimensional view of the first and second localizer images. The first and second two-dimensional views of the first and second localizer images are displayed in first and second viewing regions of a graphic prescription interface. The three-dimensional view shows the first and second localizer images relative to each other in overlapping fashion in a common viewing region of the graphic prescription interface. The method also allows a previous prescription to be displayed as a cross reference, and allows a prescription to fallback to any localizer image in a sequence of localizer images.

12 Claims, 4 Drawing Sheets

US 6,844,884 B2

MULTI-PLANE GRAPHIC PRESCRIPTION INTERFACE AND METHOD

BACKGROUND OF THE INVENTION

The field of the invention is imaging methods and systems. More particularly, the invention relates to a multi-plane graphic prescription interface and method for an imaging system.

Imaging systems are commonly employed to allow an operator to obtain images that show the interior of a structure of interest. A common application of such imaging systems is medical imaging, and a common approach for implementing such imaging systems, especially in the context of medical imaging, is magnetic resonance imaging.

When a substance such as human tissue is subjected to a uniform magnetic field (polarizing field $B_z$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_1$, which is rotating, or spinning, in the x-y plane at the Larmor frequency. The degree to which the net magnetic moment $M_z$ is tipped, and hence the magnitude of the net transverse magnetic moment $M_1$ depends primarily on the length of time and the magnitude of the applied excitation field $B_1$. A signal is emitted by the excited spins, and after the excitation signal $B_1$ is terminated, this signal may be received and processed to form an image.

When utilizing MRI to produce images, a technique is employed to obtain MRI signals from specific locations in the subject. Typically, the region which is to be imaged is scanned by a sequence of MRI measurement cycles which vary according to the particular localization method being used. The resulting set of received MRI signals are digitized and processed to reconstruct the image using one of many well known reconstruction techniques. To perform such a scan, it is, of course, necessary to elicit MRI signals from specific locations in the subject. This is accomplished by employing magnetic fields ($G_x$, $G_y$, and $G_z$) which have the same direction as the polarizing field $B_0$, but which have a gradient along the respective x, y and z axes. By controlling the strength of these gradients during each MRI cycle, the spatial distribution of spin excitation can be controlled and the location of the resulting MRI signals can be identified.

In order for an MRI system to acquire signals from a region of interest to an operator, it is necessary for the operator to first prescribe the acquisition that is to be performed, including inputting parameters such as the field of view, spacing and thickness, as well as the orientation and location of the desired image or images. In general, it is desirable for the operator to be able to optimally perform the prescription such that the prescribed image accurately encompasses the region of interest.

Graphic prescription is a technique that allows an operator to perform a prescription using graphic techniques. Typically, to perform a graphic prescription, reference localizer images are first obtained and the operator is then allowed to mark the localizer images with prescription marks such as points, lines, boxes or other shapes, and to manipulate the marks until the desired prescription is achieved. It is desirable for the prescription interface to allow the operator to operate in a manner that is efficient and that results in the operator making an accurate prescription. However, when imaging the interior of a three-dimensional structure, it is often difficult for the operator to visualize the orientation of the prescribed spatial information, particularly in double oblique cases. Even if multiple localizer images are displayed, the three-dimensional orientation of the prescribed spatial information is not always obvious and, therefore, inaccurate prescriptions often result.

SUMMARY OF THE INVENTION

In an exemplary embodiment of the invention, a method of acquiring a graphic prescription from an operator of an imaging device comprises displaying two-dimensional views of a first and second localizer images, and displaying a three-dimensional view of the first and second localizer images. The first and second two-dimensional views of the first and second localizer images are displayed in first and second viewing regions of a graphic prescription interface. The three-dimensional view shows the first and second localizer images relative to each other in overlapping fashion in a common viewing region of the graphic prescription interface.

In another exemplary embodiment of the invention, a graphic prescription interface comprises first and second interfaces. The first interface comprises a first two-dimensional view of a first localizer image and a second two-dimensional view of a second localizer image. The second interface comprises a three-dimensional view of the first and second localizer images. The three-dimensional view shows the first and second localizer images relative to each other in overlapping fashion.

The preferred embodiments of the invention significantly enhance an operator's ability to accurately perform a graphic prescription. The operator is provided with the ability to prescribe and view spatial information on multiple separate localizer images at once, and also is provided with a three-dimensional view in which the displayed localizer images and prescribed spatial information are displayed in relation to each other in three dimensions. By providing the operator with a better visual understanding of the spatial information that has been prescribed, as well as with more robust prescription techniques, more accurate prescriptions are achieved.

DESCRIPTION OF THE PREFERRED EMBODIMENT

Figure 1:
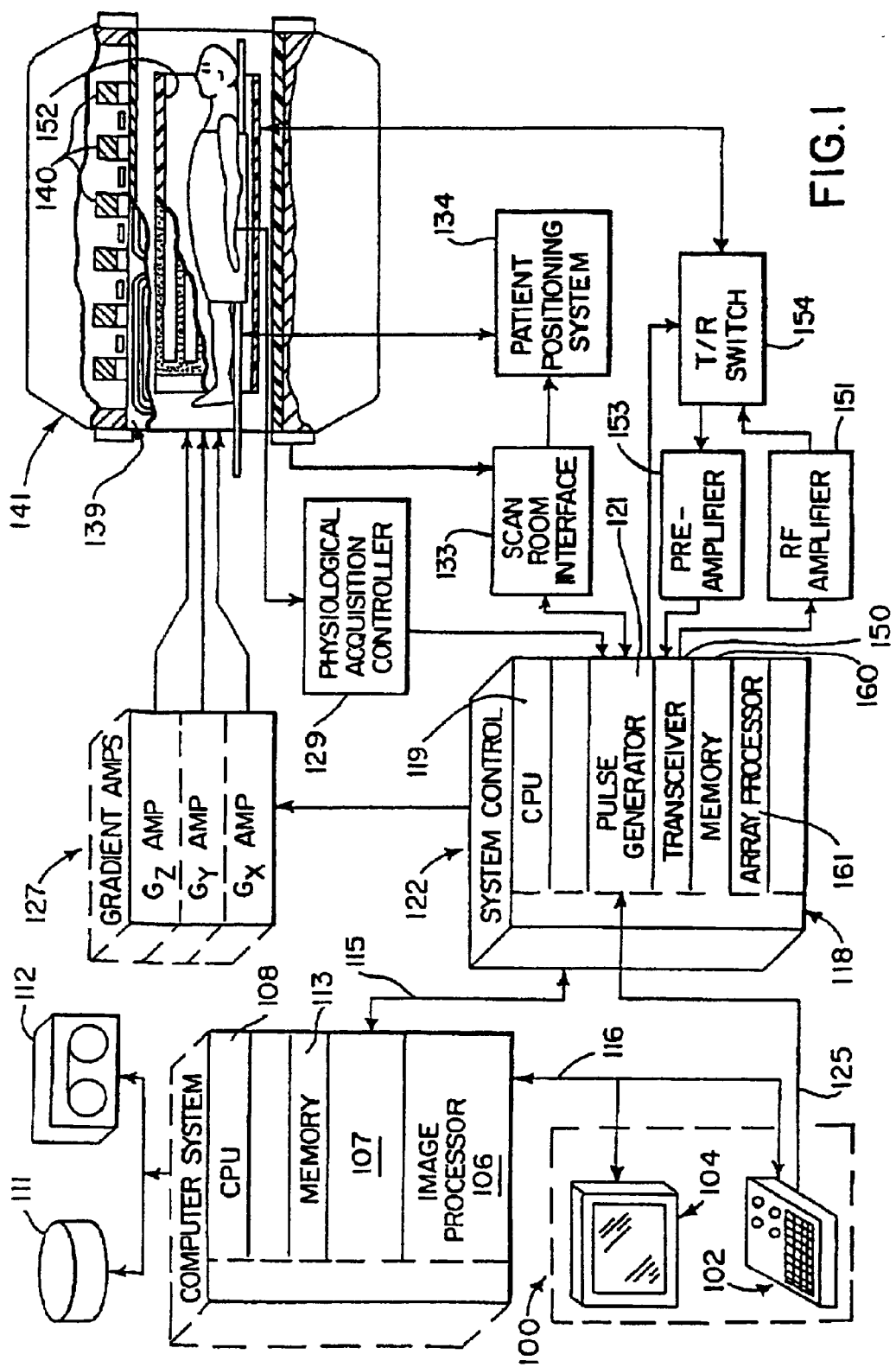
FIG. 1 is a block diagram of an MRI system which employs a preferred embodiment of the present invention.

Referring first to FIG. 1, there is shown the major components of a preferred MRI system which incorporates a preferred embodiment of the present invention. The operation of the system is controlled from an operator console 100 which includes a control panel 102 and a display 104. The control panel 102 further comprises one or more operator input devices such as a keyboard, mouse, joystick, track ball, voice control device, touch-sensitive surface of the display 104, and so on. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage device 111 and a non-volatile (e.g., optical) storage device 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified MRI signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The MRI signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
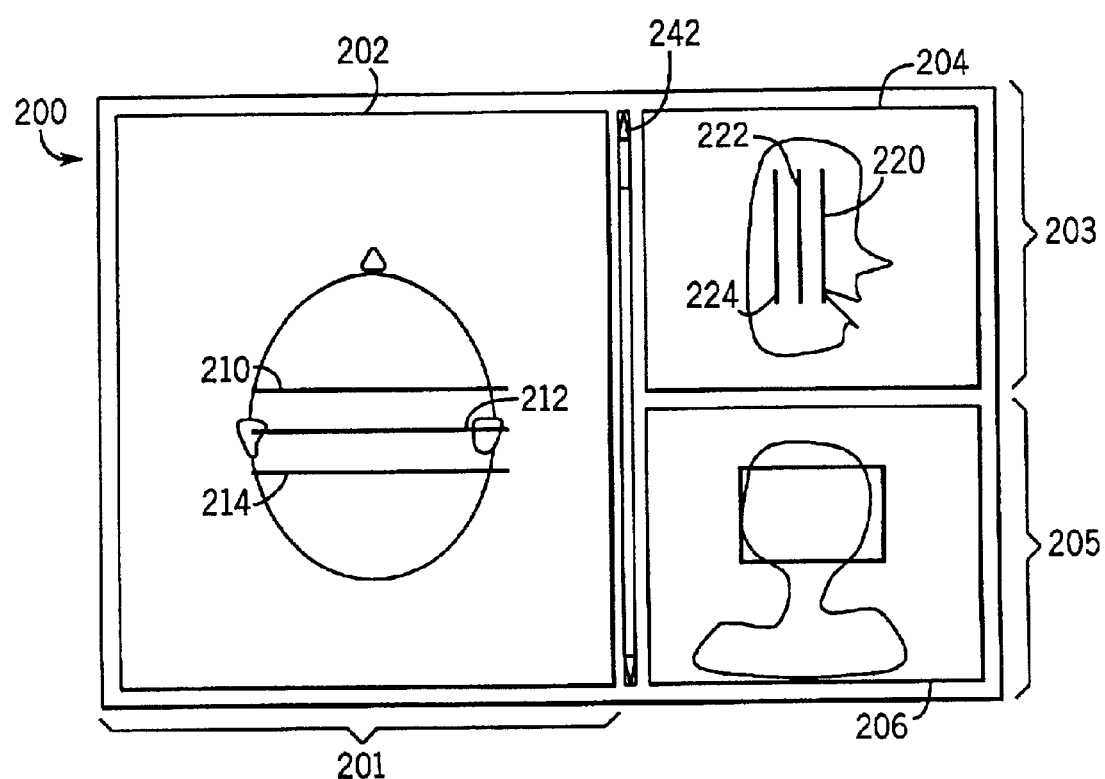
FIG. 2 is a first graphic prescription interface for the MRI system of FIG. 1, in which separate two-dimensional views of a plurality of localizer images are displayed to an operator.
Figure 3:
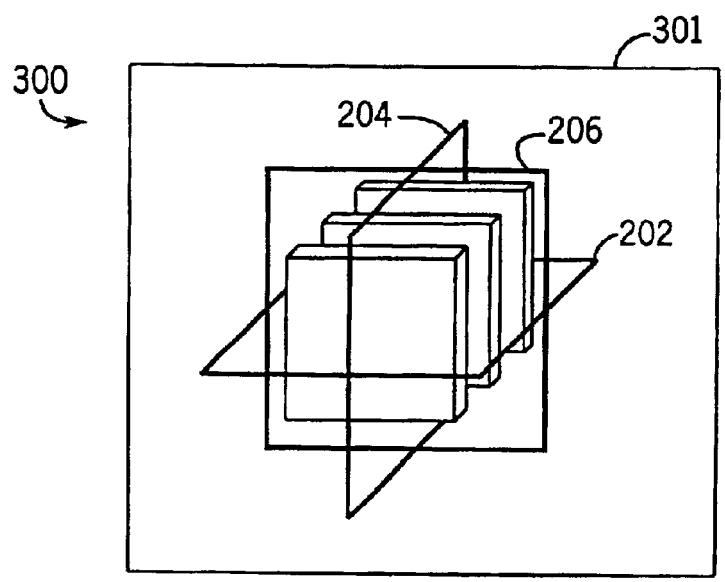
FIG. 3 is a second graphic prescription interface for the MRI system of FIG. 1, in which a three-dimensional view of the localizer images of FIG. 2 are displayed relative to each other in overlapping fashion.

Referring now to FIGS. 2 and 3, first and second graphic prescription interfaces 200 and 300 according to a preferred embodiment of the invention are illustrated. The graphic prescription interfaces 200 and 300 are used for graphic prescription in connection with the acquisition of two-dimensional images, although the invention is also applicable to graphic prescription in connection with the acquisition of three-dimensional images. Likewise, although the prescription interfaces 200 and 300 are described in connection with the MRI system of FIG. 1, the prescription interfaces 200 and 300 could also be used in connection with other types of imaging systems. The graphic prescription interfaces 200 and 300 are preferably utilized in complementary fashion to provide a single, highly robust graphic prescription interface.

Referring first to FIG. 2, the prescription interface 200 is used both to acquire prescription information from an operator as well as to display the acquired prescription information to the operator. To this end, the prescription interface utilizes the control panel 102 to receive operator inputs, and uses the display 104 to display the localizer images and prescription marks to the operator. The display 104 and hence the prescription interface 200 includes separate viewing regions 201, 203 and 205 in which one or more localizer images 202, 204 and 206 are simultaneously displayed to the operator.

The number and type of localizer images that are displayed are operator selectable. Preferably, a set of coronal localizer images, a set of sagittal localizer images, and a set of axial localizer images are acquired, with three to five images displaced along a common orthogonal axis being acquired within each set. The operator uses the control panel 102 to select a subset of these localizer images, the subset then being the displayed localizer images 202, 204 and 206. Indeed as discussed below, the operator may even scroll through multiple localizer images during the prescription. In FIG. 2, the operator has selected one image from each viewing axis (coronal, sagittal, and axial), such that the displayed localizer images include an axial localizer image 202, a sagittal localizer image 204, and a coronal localizer image 206. (Although shown as non-oblique axial, sagittal, and coronal localizer images, the localizer images 202–206 could also be oblique localizer images.) While this selection is quite valid, other selections are certainly also possible. Any number of localizer images may be selected at various oblique orientations and centered on various locations. Although mutually orthogonal localizer images are shown, the localizer images need not be mutually orthogonal.

Using the control panel 102, the system is able to acquire operator inputs that prescribe spatial information on the localizer images 202–206. Thus, as shown in FIG. 2, the localizer images 202, 204 and 206 each include graphic prescription marks which have been placed on the localizer images 202, 204 and 206 in response to operator inputs. The prescription marks indicate the spatial relationship between the localizer images 202, 204 and 206 and the images to be acquired (the prescribed images).

For example, with respect to the axial localizer image 202, a first line 210, a second 212, and a third line 214 have been placed on the localizer image 202 in response to operator inputs. The lines 210, 212 and 214 each correspond to a different image to be acquired, and represent the location on the localizer image 202 at which a respective prescribed image intersects the localizer image 202. Thus, the line 210 represents the intersection of a first prescribed image with the localizer image 202. Likewise, the lines 212 and 214 indicate the intersection of second and third prescribed images with the localizer image 202.

With respect to the sagittal localizer image 204, a plurality of additional lines including a first line 220, a second line 222, and a third line 224 have been placed on the localizer image 204 in response to operator inputs. The lines 220, 222 and 224 respectively correspond to the first, second and third prescribed images as discussed above in connection with the lines 210, 212 and 214, and represent the location on the localizer image 204 at which a respective prescribed image intersects the localizer image 204. Thus, the line 220 represents the intersection of the first prescribed image with the localizer image 204. Likewise, the lines 222 and 224 indicate the intersection of the second and third prescribed images with localizer image 204. It is therefore seen how the prescription lines 210–214 and 220–224 indicate, with respect to the localizer images 202 and 204, where the next three images are to be acquired.

With respect to the coronal localizer image 206, a rectangle 230 has been placed on the localizer image 206 in response to operator inputs. The rectangle 230 represents the projection of the first, second and third prescribed images on the coronal localizer image 206. Conceivably, the rectangle could also be used to represent the intersection of one of the first, second and third prescribed images with the localizer image 206, but the prescribed images and the localizer 206 may not intersect depending on the position and orientation of the coronal localizer image relative to the prescribed images.

Because the prescribed images are coronal images in the illustrated example, the coronal localizer image 206 provides the ability to view a two-dimensional localizer image having the same orientation as the prescribed images. With this arrangement, the operator is able to change the location and the field of view of the prescribed image, and the graphic prescription interface 200 is able to provide the operator with a clear visualization of the prescription that has been performed. Additionally, this arrangement allows the operator to move the prescribed image to any location on the coronal localizer image 206 without regard to where the sagittal and axial localizer images 202 and 204 were acquired.

As has been described, in the illustrated embodiment, the localizer images 202 and 204 have prescription marks that represent the intersection of the prescribed images with the localizer images 202 and 204, whereas the localizer image 206 has a prescription mark that represents the projection of the prescribed images on the localizer image 206. Of course, whether the prescription marks indicate the intersection of a prescribed image with a localizer image or the projection of the prescribed image on the localizer image will depend on the orientation of the prescribed image as well as the orientation of the localizer image upon which the prescription marks are placed. It should also be noted that other types of prescription marks besides lines and boxes could be used to indicate the spatial relationship between the prescribed images and the localizer images in some other way.

The spatial information that is prescribed on one localizer image is simultaneously displayed on all affected localizer images. Therefore, as the location or orientation of the prescribed spatial information changes, the changes are immediately displayed on the remaining affected localizer images. For example, if the field of view is changed in one direction on the localizer image 206, then this change is displayed on one of the localizer images 202 and 204 in the form of a change in the length of one of the prescription lines.

In addition, the prescription interface 200 preferably allows the operator to change the displayed localizer image to another localizer image to permit the operator to visualize how the prescribed spatial information intersects with anatomy in different locations. To this end, the prescription interface 200 preferably includes a scroll interface which, in the disclosed embodiment, comprises a scroll bar 242. Thus, while the operator is performing the prescription, it may be the case that certain localizer images only contain part of the information that is needed to perform a complete prescription, with all of the information being spread out over multiple localizer images. In this situation, the operator can use the scroll bar 242 to cause the prescription interface 200 to scroll back and forth between various sagittal localizer images such that a sequence of sagittal localizer images is displayed. This allows the operator to prescribe information using multiple sagittal localizer images and to visualize how the prescribed spatial information intersects with anatomy in different locations. In this way, the graphic prescription interface 200 ensures sufficient coverage of the desired anatomy during prescription.

The scroll interface of FIG. 2 also preferably implements a fallback feature in which the operator is allowed to perform a prescription using one localizer image in a sequence of localizer images, and then have the prescription fall back to any other one of the localizer images in the sequence of localizer images. For example, when prescribing a sagittal image of a patient's shoulder using a sequence of coronal localizer images, the following sequence of events may occur. First, operator inputs are acquired that select a first coronal localizer image acquired from a first location in the anterior/posterior direction. The first localizer image is selected on the basis that a particular area of anatomy is more clearly visible in the first localizer image than in the remaining localizer images. Then, operator inputs are acquired that prescribe an image to be acquired using the first localizer image. Next, operator inputs are acquired that select a second coronal localizer image acquired from a second location in the anterior/posterior direction. The second localizer image is selected on the basis that the operator wants the prescribed sagittal image to be centered (in the anterior/posterior direction) about the second location. Finally, operator inputs are acquired that indicate that the prescription performed with respect to the first localizer image should fall back to the second localizer image. This allows the operator to perform the prescription using a first localizer image in a sequence of localizer images, and then use a second localizer image to indicate where the prescribed image should be centered. This is particularly useful in situations in which all of the localizer images are acquired along a single common axis.

Referring now to FIG. 3, in addition to the two-dimensional interface of FIG. 2, a three-dimensional graphic prescription interface 300 is preferably also utilized. In the graphic prescription interface 300, the axial localizer image 202, the sagittal localizer 204, and the coronal localizer image 206 are again displayed to the operator. However, whereas in the graphic prescription interface 200 displays separate two-dimensional views of the localizer images 202–206, the graphic prescription interface 300 displays a single three-dimensional view of the localizer images 202–206. In this view, the localizer images 202, 204 and 206 and the prescribed spatial information are displayed in relation to each other in overlapping fashion in a common viewing region 301. The view that is provided by the prescription interface 300 is referred to as a three-dimensional view because the view appears three-dimensional to the operator (e.g., in the same way that FIG. 3 has a three-dimensional appearance), even though the view is in fact provided on a generally two-dimensional viewing surface of the display 104.

In FIG. 3, the localizer images 202–206 are shown only schematically for sake of clarity. In the preferred embodiment, however, the actual localizer images are displayed to the operator in order to give the operator the impression that a three-dimensional cross section of the patient's anatomy is being viewed. Three-dimensional image slabs are used to represent the prescribed images rather than display the lines 212, 214, 216, 222, 224 and 226 and the rectangle 230.

The graphic prescription interface 300 complements the graphic prescription interface 200 by providing a three-dimensional view of the localizer images 202–206 and the spatial information that has been prescribed. Additionally, the prescription interface 300 allows the operator to provide inputs that cause rotation of the entire three-dimensional view, including the localizer images and the prescribed spatial information. This permits the operator to view the prescription from any perspective as the three-dimensional view is rotated, thereby providing a very intuitive understanding of orientation, especially in cases of double oblique prescriptions.

Because the prescription interface 300 is used in combination with the prescription interface 200, there is no particular need to allow the operator to use the prescription interface 300 to prescribe spatial information on the localizer images 202–206 and, in fact, it is preferred to provide this ability exclusively through the prescription interface 200 for reasons of simplicity. On the other hand, alternative implementations are certainly also possible. For example, the prescription interface 300 could be used to allow the operator to accurately prescribe spatial information in three dimensions by having additional indicators that show the position of the prescription marks relative to each of the localizer images 202–206 individually. Alternatively, an explicit prescription interface may be used instead of or in combination with the prescription interface 200 to allow the operator to prescribe spatial information explicitly (e.g., by entering values via a keyboard) rather than graphically. In this case, the graphic prescription interface 300 would be used to provide a visualization of the spatial information prescribed using the explicit prescription interface.

Figure 4:
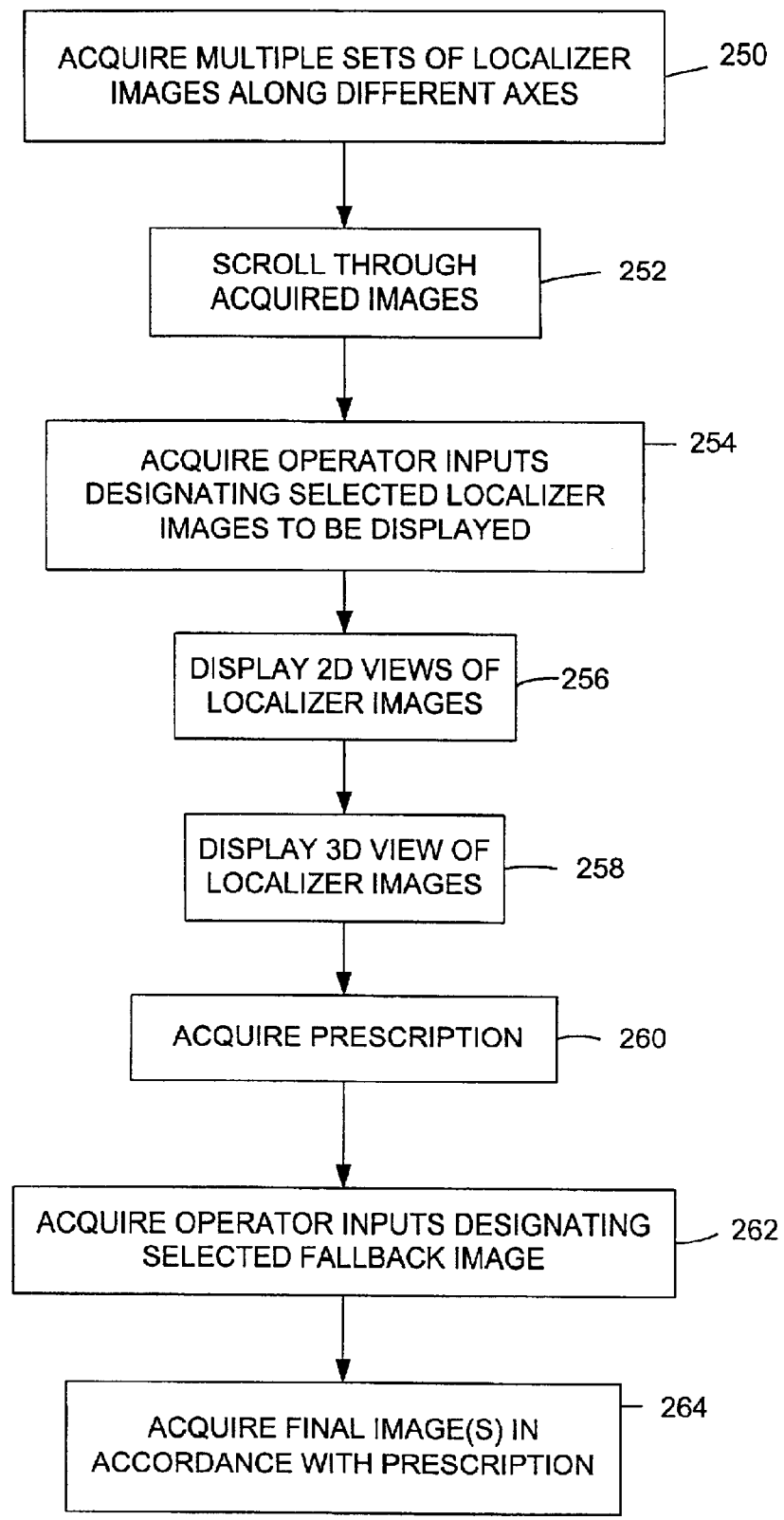
FIG. 4 is a prescription process used in connection with the prescription interface of FIGS. 2–3.

FIG. 4 is a prescription process used in connection with the prescription interface of FIGS. 2–3. At step 250, the MRI system first acquires a plurality of localizer images. The different localizer images show the structure of interest from different perspectives (e.g., three different perspectives if coronal, axial, and sagittal localizer images are acquired). At step 252, operator inputs are acquired by the scroll interface that cause the prescription interfaces 200 and/or the prescription interface 300 to scroll through and display the localizer images acquired during step 250. At step 254, the system acquires operator inputs that designate selected localizer images 202, 204 and 206 to be used for graphic prescription.

At steps 256 and 258, two-dimensional and three-dimensional views of the localizer images 202, 204, and 206 is displayed as previously discussed in connection with FIGS. 2–3, respectively. Steps 256 and 258 are shown as two separate steps, although in practice steps 256 and 258 are preferably performed simultaneously.

At step 260, once an initial set of localizer images is selected and displayed, the prescription is acquired and the resulting prescription marks displayed. Step 260 preferably proceeds in the following manner. First, a particular one of the displayed localizer images is selected in response to operator inputs. When one of the localizer images is selected, a default prescription (as indicated by one or more prescription marks) appears on the localizer image (e.g., a line automatically appears on the localizer image showing the default prescription). At the same time, the default prescription is also displayed on the remaining localizer images. The operator is then allowed to manipulate the prescription marks in any desired manner. For example, assuming lines are used as prescription marks, the operator is allowed to move the lines to a new location on the localizer image as well as to change the orientation and/or the length of the lines. By default, the lines are oriented such that the default prescription results in a non-oblique image, however, the operator is permitted to tilt or rotate the lines to obtain oblique orientations. From the operator's perspective, a line can be rotated by clicking on a portion of the line and rotating the line to a new orientation, although it is of course actually the prescription interface 200 that causes the line to rotate in response to operator inputs. Since images are typically acquired as a stack of image slices, the prescription marks are preferably caused to move/rotate as a group.

At the same time, the graphic prescription interface 300 provides a three-dimensional view of the localizer images 202–206 and the spatial information that has been prescribed. Additionally, the prescription interface 300 allows the operator to provide inputs that cause rotation of the entire three-dimensional view, including the localizer images and the prescribed spatial information.

At step 262, if a fallback is to be performed, then operator inputs are acquired that select a fallback image and that indicate that the prescription performed with respect to one localizer image should fall back to a another localizer image. As previously discussed, this feature allows the operator to perform the prescription using one localizer image in a sequence of localizer images, and then use the other localizer image to indicate where the prescribed image should be centered. Of course, if a fallback is not to be performed, then step 262 is skipped.

Finally, at step 264, after the prescription is acquired, the prescription is provided to the remainder of the MRI system, which uses the prescription to acquire one or more images in accordance with the previously-acquired prescription. Advantageously, with the preferred interfaces 200 and 300, because multiple localizer images having different orientations are displayed, it is possible to obtain several degrees of prescriptive freedom through utilization of additional images. The operator is not limited to manipulation of the prescription marks within a single plane, and, therefore, a very robust prescription interface is achieved. Additionally, visualization is enhanced by providing the operator with the ability to view the prescribed image from multiple orientations. The graphic prescription interface 300 of FIG. 3 complements the graphic prescription interface 200 by providing a rotatable three-dimensional view of the localizer images 202–206 and the spatial information that has been prescribed.

Figure 5:
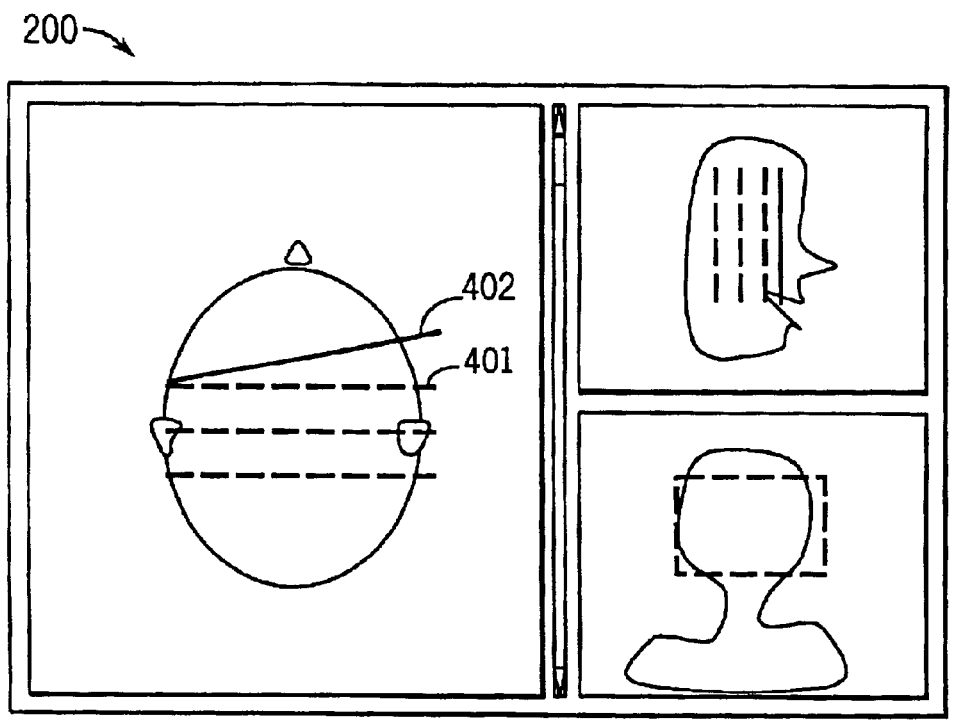
FIG. 5 shows the operation of the graphic prescription interface of FIG. 2 in a prescription cross-reference mode of operation.

Referring now to FIG. 5, FIG. 5 shows the graphic prescription interface of FIG. 2 in a prescription cross reference mode of operation. The prescription cross reference mode of operation allows the operator to view a previous prescription while performing a current prescription. This allows the previous prescription to be used as a reference for recreating a previous prescription or for slightly adjusting the location of the spatial information from a previous prescription for a new acquisition. Thus, in FIG. 5, a first prescription line 401 and a second prescription line 402 are shown. The prescription line 401 shows a previous prescription and is shown as a dashed line. The prescription line 402 has been rotated slightly with respect to the prescription 401 such that the prescribed image is a slightly oblique coronal image. Therefore, when the operator wants to acquire an image with a slightly different orientation than a previously acquired image, the prescription line 401 provides the operator with an indication of the spatial relationship between the prescribed image and the previously acquired image. The increases the operator's ability to accurately prescribe the new image.

While the embodiments and application of the invention illustrated in the figures and described above are presently preferred, it should be understood that these embodiments are offered by way of example only. Accordingly, the present invention is not limited to a particular embodiment, but extends to various modifications that nevertheless fall within the scope of the appended claims.

What is claimed is:

1. A graphic prescription interface comprising:
    a first interface, said first interface comprising a first two-dimensional view of a first localizer image and a second two-dimensional view of a second localizer image;
    a second interface, said second interface comprising a single three-dimensional view including said first and second localizer images, said three-dimensional view showing said first and second localizer images relative to each other in overlapping fashion in three dimensional space.

2. A graphic prescription interface according to claim 1, wherein prescription marks are displayed on said first and second two dimensional views of said first and second localizer images that indicate a desired location and desired orientation from which a prescribed image is to be acquired, and wherein additional prescription marks are displayed on said three-dimensional view of said first and second localizer images that also indicate said desired location and said desired orientation from which said prescribed image is to be acquired.

3. A graphic prescription interface according to claim 2, wherein at least one of said first and second localizer images comprises a first prescription mark that indicates an intersection of said prescribed image with said at least one localizer image.

4. A graphic prescription interface according to claim 3, wherein at least one of said first and second localizer images comprises a second prescription mark that indicates a projection of said prescribed image on said at least one localizer image.

5. A graphic prescription interface according to claim 4, wherein at least one of said first and second localizer images comprises third and fourth prescription marks, said third prescription mark being indicative of a spatial relationship between said prescribed image and said at least one localizer image, and said fourth prescription mark being indicative of a spatial relationship between said prescribed image and a previously acquired image.

6. A graphic prescription interface according to claim 4, wherein one of said first and second localizer images is one of a plurality of localizer images that are spaced along a common axis, and wherein said graphic prescription interface includes a scroll interface, said scroll interface permitting the operator to select between different ones of said localizer images disposed along said common axis, including a first localizer image upon which spatial information is prescribed and a second localizer image that is selected to indicate the desired location of said prescribed image along said common axis.

7. A graphic prescription interface according to claim 1, wherein said three-dimensional view of said first and second localizer images is rotatable, such that said first and second localizer images are viewable from different perspectives as said three-dimensional view is rotated.

8. A graphic prescription interface according to claim 3, wherein said first and second localizer images are acquired using a magnetic resonance imaging system, and wherein said graphic prescription pertains to images to be acquired using said magnetic resonance imaging system.

9. A graphic prescription interface comprising:
    means for acquiring operator inputs;
    means for displaying first and second localizer images, said first and second localizer images showing a structure of interest from different perspectives, said first and second localizer images being displayed such that spatial information prescribed on one of said first and second localizer images as a result of said operator inputs is viewable on the other of said first and second localizer images, and such that changes made in the spatial information prescribed on one of said first and second localizer images are viewable on the other of said first and second localizer images, and wherein said means for displaying displays a first two-dimensional view of said first localizer image, a second two-dimensional view of said second localizer image, and a single three-dimensional view including said first and second localizer images, said three-dimensional view showing said first and second localizer images relative to each other in overlapping fashion in three dimensional space.

10. A method of acquiring a graphic prescription from an operator of a magnetic resonance imaging device, the method comprising:
    displaying a first two-dimensional view of a first localizer image and a second two-dimensional view of a second localizer image, said first and second two-dimensional views of said first and second localizer images being displayed in first and second viewing regions of a graphic prescription interface;
    displaying a single three-dimensional view including said first and second localizer images, said three-dimensional view showing said first and second localizer images relative to each other in overlapping fashion in three dimensional space in a common viewing region of said graphic prescription interface;
    acquiring operator inputs that prescribe spatial information on one of said first and second localizer images and that indicate a desired location and a desired orientation from which a prescribed image is to be acquired;

displaying said prescribed spatial information on said first and second two-dimensional views of said first and second localizer images and on said three-dimensional view of said first and second localizer images, including displaying at least one prescription mark that indicates an intersection of said prescribed image with said at least one localizer image, and at least one prescription mark that indicates a projection of said prescribed image on said at least one localizer image;

acquiring said prescribed image using said magnetic resonance imaging system, said acquired prescribed image portraying a location of said structure of interest and portraying said location from an orientation both of which are determined by said prescribed spatial information.

11. A method according to claim 10, wherein at least one of said first and second localizer images comprises first and second prescription marks, said first prescription mark being indicative of a spatial relationship between said prescribed image and said at least one localizer image, and said second prescription mark being indicative of a spatial relationship between said prescribed image and a previously acquired image.

12. A method according to claim 10 wherein, during said operator inputs acquiring step, the operator inputs prescribe spatial information on one of a plurality of localizer images that form a sequence of localizer images displaced along a common axis, one of said first and second localizer images being one of said plurality of localizer images, and wherein the method further comprises scrolling through said plurality of localizer images in response to operator inputs such that said plurality of localizer images are displayed to the operator in sequence;

acquiring additional operator inputs that select an additional one of the images in said sequence of images, said selected image indicating the desired location of said prescribed image along said common axis.

* * * * *